US007193722B2

(12) United States Patent
Boogaarts et al.

(10) Patent No.: US 7,193,722 B2
(45) Date of Patent: Mar. 20, 2007

(54) LITHOGRAPHIC APPARATUS WITH DISTURBANCE CORRECTION SYSTEM AND DEVICE MANUFACTURING METHOD

(75) Inventors: Martinus Godefridus Helena Boogaarts, Sint Michielsgestel (NL); Hans Butler, Best (NL); Henrikus Herman Marie Cox, Eindhoven (NL); Martinus Agnes Willem Cuijpers, Veldhoven (NL); Jan Jaap Kuit, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 267 days.

(21) Appl. No.: 10/747,617

(22) Filed: Dec. 30, 2003

(65) Prior Publication Data

US 2005/0139790 A1 Jun. 30, 2005

(51) Int. Cl.
*G01B 9/02* (2006.01)
*G03B 27/68* (2006.01)
(52) U.S. Cl. ........................ 356/500; 355/52
(58) Field of Classification Search .................. 355/52, 355/53, 72; 356/498, 500; 250/548
See application file for complete search history.

(56) References Cited

U.S. PATENT DOCUMENTS

| 5,511,930 A * | 4/1996 | Sato et al. ................ 356/498 |
| 6,842,256 B2 * | 1/2005 | Hill ............................ 356/500 |
| 2003/0202165 A1 * | 10/2003 | Shiraishi ..................... 355/53 |

FOREIGN PATENT DOCUMENTS

| EP | 0 557 100 A1 * | 8/1993 |
| WO | WO 98/40791 | * 9/1998 |

* cited by examiner

*Primary Examiner*—Gregory J. Toatley, Jr.
*Assistant Examiner*—Patrick Connolly
(74) *Attorney, Agent, or Firm*—Pillsbury Winthrop Shaw Pittman LLP

(57) ABSTRACT

A lithographic projection apparatus is presented, which includes a housing, which comprises therein a first exposure system that has at least one movable part (e.g. a movable first substrate holder or a movable second substrate holder in a twin stage apparatus). The apparatus also includes a position disturbance correction system for correcting a position of the first substrate holder with respect to the patterned projection beam due to the influence of gas pressure differences or gas movements, caused by movements of the movable part. A related device manufacturing method is also presented in which, during the exposure of a first substrate, the position thereof is corrected by means of position disturbance correction system.

28 Claims, 5 Drawing Sheets

LITHOGRAPHIC APPARATUS WITH DISTURBANCE CORRECTION SYSTEM AND DEVICE MANUFACTURING METHOD

BACKGROUND OF THE INVENTION

1. Field of the Invention

The present invention relates to a lithographic apparatus and a device manufacturing method.

2. Description of the Related Art

A lithographic apparatus is a machine that applies a desired pattern onto a target portion of a substrate. Lithographic apparatus can be used, for example, in the manufacture of integrated circuits (ICs). In that circumstance, a patterning devices, such as a mask, may be used to generate a circuit pattern corresponding to an individual layer of the IC, and this pattern can be imaged onto a target portion (e.g. comprising part of, one or several dies) on a substrate (e.g. a silicon wafer) that has a layer of radiation-sensitive material (resist).

In general, a single substrate will contain a network of adjacent target portions that are successively exposed. Known lithographic apparatus include so-called steppers, in which each target portion is irradiated by exposing an entire pattern onto the target portion in one go, and so-called scanners, in which each target portion is irradiated by scanning the pattern through the projection beam in a given direction (the "scanning"-direction) while synchronously scanning the substrate parallel or anti-parallel to this direction.

It has been found that the position of the stage or substrate holder (i.e., substrate holder) with respect to the projection beam is disturbed under many circumstances. This disturbance was thought largely due to mechanical influences, because moving parts, such as a moving measuring stage in a two stage apparatus, would exert forces on, for example, the substrate holder through the medium of the mounts, the suspension, and in general through the (mechanical) rest of the apparatus. In fact, suspension and mechanical decoupling techniques were much improved, but still a residual disturbance remained. This residual disturbance may limit the minimum feature size and the minimum overlay error during projection.

SUMMARY OF THE INVENTION

Principles of the present invention, as embodied and broadly described herein, provide for a lithographic apparatus with a reduced residual position disturbance. In one embodiment, the apparatus comprises a housing, which includes a first exposure system that has at least one movable part and that comprises: a radiation system constructed for providing a projection beam of radiation, a support structure for supporting a patterning device that patterns the beam of radiation, a first substrate holder for holding a substrate, a projection system constructed for projecting the patterned beam onto a target portion of the substrate, a positioning device for positioning the first substrate holder relative to the projection system and a first control unit constructed for controlling said positioning device, wherein the apparatus further comprises a position disturbance correction system constructed to counteract a disturbance of a position of the first substrate holder with respect to the projection system, which disturbance is caused by gas movements induced by movement of the movable part.

The inventors have discovered that it is the change in the gas pressure, or the movement of air or other gas inside the lithographic apparatus, which is an important cause of residual influences on the positioning of movable parts inside the apparatus. The gas thus set in motion will interact, e.g. through friction, with the exposure stage or the projection system. This will cause deviations from the ideal calculated position of the one with respect to the other.

As such, the invention therefore generally relates to means constructed for minimizing the influence of these air movements on the position of a substrate holder with respect to the projection system. The invention thus resides in providing correction means to counteract the position disturbance due to such gas movements, or gas pressure changes. It is to be noted that, for the purpose of this application and for brevity, gas movements and gas pressure changes are deemed to include one another.

The movable part may be any movable part within the housing that causes gas pressure changes that are able to disturb the mutual position of the (first) substrate holder with respect to the projection system. In particular, the at least one movable part comprises at least one of the support structure and the first substrate holder. These movable parts are present in e.g. a lithographic step-and-scan apparatus, and these will cause relatively large gas movements, especially because of throughput demands and hence speed demands. The influence of these movements, i.e. of inherently present movable parts of the apparatus, is not negligible, and counteracted with the measures according to the invention.

In a particular embodiment, the housing comprises at least one additional movable part, which is movable by means of a second control unit. In this apparatus, the presence of such an additional movable part causes influences on the position of e.g. the first substrate holder, which generally do not relate to any movement of the first substrate holder or control thereof. In other words, the presence of such an additional movable part, and of course its actual movements, may influence the position of the first substrate holder even more unpredictable. Hence, providing means for correcting this influence are even more important than for the case where the movable part is e.g. the first substrate holder itself.

Advantageously, the additional movable part comprises at least one of a second exposure stage that has at least a movable second substrate holder, and a measuring stage for measuring a property of a substrate, that has at least one of a movable substrate measuring table and a movable measuring unit. Throughout all of the present application, it is advantageous when a second stage, be it a second substrate holder or a measuring stage, is considered to be the (or one) additional movable part. For brevity's sake this will not be repeated for every other embodiment yet to be mentioned.

This embodiment relates to two stage apparatus, which offer increased throughput, but are more susceptible to position disturbances due to the presence of these two stages. A particular type of lithographic apparatus comprises two stages for processing wafers, a first stage for projection of a desired pattern onto a first wafer and a second stage for measuring a surface property of a second wafer.

On the first stage, the projection stage, a desired pattern is projected onto a wafer, and on the second stage, a surface property is measured, in particular but not exclusively a height map is determined by scanning the surface of the wafer. Note that the ordinals "first" and "second" do not relate to a specific temporal order, since in practice a wafer will first be measured on the second stage, and subsequently be illuminated on the first stage.

The measuring involves scanning the surface of a wafer, which implies moving the second stage relative to the measuring system. Also, the positions of substrate markers on the wafer may be determined by means of an alignment system, involving stepwise movements of the second stage. Also, projecting the desired pattern onto the first wafer implies movement of the first stage relative to the projection system. The present invention can offer effective position correction for apparatus like these, with two stages. Nevertheless, apparatus with e.g. two exposure stages, or combinations with even more stages will benefit likewise of the present invention.

In an advantageous embodiment, the position disturbance correction system comprises a separation wall which is positionable between the additional movable part and at least one of the first substrate holder and the patterning device. Herein, the word 'between' should be interpreted to include the situation that the separation wall crosses the path along which gas that is set in motion will travel. In other words, it is not necessary that the separation wall is present in a position which is "geographically" between said two spaces, but it is preferred that the separation wall is present in a position that it can effectively block at least a part of the flow of air caused by a moving part inside the apparatus. Hence, the separation wall could also be present inside some zigzag-conduct between the first and second spaces. Such a zigzag shape is helpful in damping the air movements inside it. Note that the first and second space may be parts of one big space, in which case the first space may be considered to be a part of the big space located on a first side of the separation wall, and the second space is another part of the big space located on a second side of the separation wall.

Advantageously, the separation wall comprises an acoustic damping material. Such material can effectively damp gas movements. Note that the acoustic damping material may also be applied to any other wall within the housing, to help reduce gas movements further.

A generalized version of the separation wall are air damping systems. These air damping systems, or acoustic damping systems, serve to slow down or remove pressure variations from air which passes along them or through them. Such air damping systems may comprise curtains, foam-like material, "feather"-like objects etc.

In an advantageous embodiment, the first substrate holder is located in a first space, and the additional movable part is located in a second space within the housing, and the separation wall is movable into a first position in which said separation wall substantially seals said first space with respect to said second space, and into a second position in which swapping of the first and second substrate holder is possible. Providing such a movable separation wall prevents air movements caused by a moving first object (e.g. second substrate holder or holder) from reaching a second object (e.g. first substrate holder or (first) patterning device) in a very effective way. The separation wall, or more generally the separation system, i.e. any object capable of decreasing the air communication between a space around the first substrate holder and a space around the second substrate holder, should preferably be not so flexible that air movements may be passed through the separation wall itself.

In another embodiment, the first and/or the second control unit are designed to maintain a predetermined minimum distance between the first substrate holder and the additional moving part at least during projecting of the patterned beam. Herein, use is made of a predetermined minimum distance in order to minimize the position disturbance, and hence to correct position disturbances to a certain degree. Any gas movement will fade with distance, and the larger the distance, the more these movements will have faded away.

Advantageously, the predetermined minimum distance is equal to at least 50% of a time averaged distance between the first substrate holder and the additional movable part at least during projecting of the patterned beam, and even more advantageously it is substantially equal to said time averaged distance. In practice, the first substrate holder and the additional movable part will move, and they will often move independent of each other. In this case their mutual distance will change in time. The time averaged distance may then be determined by measuring the distance between the first substrate holder and the additional movable part during projecting of the beam onto the substrate, i.e. during the period of time in which position disturbances matter. Preferably, the time averaged distance, and thus also the predetermined distance, is selected as large as possible, the time averaged value being the theoretical maximum, which latter case corresponds to synchronized movements of the first substrate holder and the additional movable part.

The position disturbance correction system is constructed to reduce a speed of the additional movable part to a speed value, which is less than a predetermined maximum speed value, when a distance between the first substrate holder and the additional movable part is less than a predetermined minimum distance value.

Note that, until now, the movements of the first substrate holder and the additional movable part, such as the second substrate holder, were largely independent. This means that it is very well possible that during a certain phase of the exposure the first substrate holder and the second substrate holder are very close to each other, with the risk of maximum influence of movement of the second substrate holder, while during another phase both substrate holders are very far removed from each other. It is considered advantageous to construct the first and second control units to prevent this distance from becoming too small. In other words, the movements of the substrate holders are designed such that a situation in which the substrate holders come relatively close to each other is prevented.

The first and second control units may comprise a position control unit comprising e.g. a computer connected to positioning motors for the substrate holders. The first and second control units may also comprise some mechanical mechanism constructed for limiting the distance between the substrate holders to a certain minimum distance.

Advantageously, the position disturbance correction system is constructed to reduce a speed and/or an acceleration of the additional movable part to a speed value, an acceleration value, respectively, which is less than a predetermined maximum speed value, maximum acceleration value, respectively, when a distance between the first substrate holder and the additional movable part is less than a predetermined minimum distance value.

Advantageously, the maximum speed value is smaller than a time averaged value of the speed of the additional movable part during projecting of the patterned beam onto the substrate in the first exposure system. Similarly, the maximum acceleration value is smaller than a time averaged absolute value of the acceleration of the additional movable part during projecting of the patterned beam onto the substrate in the first exposure system. Both for the speed and the acceleration, the values may be averaged over the time of exposing the substrate(s). The idea behind it is to reduce the speed and/or acceleration of movable parts when they are near the first substrate holder, or the patterning device, which should also be kept free from position disturbances.

Herein the position disturbance correction system, which may comprise first and second control units constructed for the first substrate holder, the second substrate holder, respectively, are designed and constructed for carrying out a method in which the speed of at least the second substrate holder is limited to a certain predetermined maximum speed value at least when the distance between the first substrate holder and the second substrate holder is below a certain minimum distance value. In this way, the possible influence of air movements caused by the second substrate holder is minimized when the distance between the substrate holders is relatively small.

Similar considerations apply in an embodiment in which an acceleration of the second substrate holder is limited to a certain predetermined maximum acceleration value when the distance between the first substrate holder and the second substrate holder is below a certain minimum distance value. The expression 'absolute acceleration' indicates an absolute value of the acceleration, that is without looking at direction or sign (i.e. acceleration or deceleration). Both the average speed and the average acceleration relate to the movements during measuring of a surface property of the second substrate and all other movements carried out by the second substrate holder.

In an advantageous embodiment of the invention, a wall, which at least partly surrounds a first space in which the movable part is located, comprises at least one aperture which is not intended for transport of the movable part therethrough, wherein the first space communicates with a second space behind that wall, as seen from the movable part. In this embodiment there is provided the possibility of moving air escaping through a hole in the wall that surrounds the first and/or the second substrate holder. In this way the influence of the moving air on the substrate holder will diminish. More generally, it would be beneficial to increase the volume of the apparatus, at least regarding the space in which the substrate holders are located. Often, this is not possible. In those cases, it is advantageous to provide one or more holes in the wall, in order to make the volume as seen by the moving air larger. It is advantageous to provide the holes in the vicinity of the additional movable part(s), such as a second substrate holder, in order to prevent much of the air movement to reach the first substrate holder altogether. Holes in the vicinity of the first substrate holder are advantageous in preventing the build-up of locally increased or decreased air pressure. The holes will advantageously have a cross-sectional area of at least 0,5 cm$^2$, while larger holes will have a more positive influence. The number indicated is however relative, in that a large number of small holes may have a similar influence as one or a few bigger holes or apertures. Note that in all of the present application, the term air is intended to comprise any gas or gas mixture present in the apparatus, e.g. nitrogen, conditioned air, noble gases etc.

Advantageously, a second space behind the wall is present, which second space will act as a kind of buffer, in that it can absorb much of the influence of the air movements. This second space may be some kind of space already present in the apparatus, or added to the apparatus, such as a space inside a double outer wall. Advantageously, the second space is the external environment of the apparatus, which offers the largest possible additional space. Especially in the case in which in the apparatus an overpressure is maintained with respect to the pressure in the second space, and in particular the external environment of the apparatus, such an open communication with the second space need not cause problems with respect to dust ingress etc.

In an advantageous embodiment, the lithographic projection apparatus further comprises gas transport mechanism constructed for transporting a flow of gas past the substrate during projection of the patterned beam onto the substrate, wherein the position disturbance correction system comprises gas suction mechanism constructed for sucking gas out of the flow after the flow has passed said substrate. This embodiment relates in general to the situation in which a flow of gas is present in the apparatus. In particular, said flow of gas may be present past a substrate, and still more particular past the first substrate. Such a flow may be used e.g. for the purpose of temperature control, or to provide a body of gas with known properties, which is important in e.g. the case of interferometer measurements. Other positions of gas flows are not excluded, however. It is advantageous when such air flow is prevented from building up inside the apparatus, and even more advantageous when such gas is sucked out of the apparatus. For example already present vacuum suction systems, such as those for holding the substrate in position, may be used for providing a suction action.

Another advantageous embodiment is characterized in that the position disturbance correction system comprises a planar motor for moving at least one movable part. A planar motor is a type of drive mechanism which is known per se. It is based on electromagnetic principles, and the motor comprises (electro)magnets in one part, preferably the stator plate in the apparatus, and one or more coils in the other part, preferably the moving part such as the substrate holder. By appropriately controlling the magnetic fields of the (electro) magnets, it is possible to "drag" the substrate holder with the coils from one place to another. Some advantages are that this type of motor may be made very flat, such as to present as small a front area as possible in order to have a low air resistance. Other types of motors are not excluded however, motor types with small dimensions being preferred for the above reason.

More generally, it is advantageous for moving parts, in particular the first and/or second substrate holder, to have a low air resistance. On the one hand, this will cause less air movements and hence less disturbance of the position of other parts in the apparatus, while on the other hand the susceptibility to such gas movements is also decreased. Preferably, at least one external edge and/or corner of the first and/or second substrate holder is substantially rounded off. This means that a ratio of a radius of curvature of said edge or corner and a dimension of a corresponding surface limited by that edge or corner is preferably between 0.05 and 1, more preferably between about 0.1 and 1. Other techniques for lowering air resistance, and in particular a drag coefficient may also be applied to the substrate holders.

In another preferred embodiment, the position disturbance correction system comprises at least one loudspeaker for moving gas at least in a space surrounding the movable part, again in particular the first and/or a second substrate holder. The at least one speaker may be used to produce a gas flow that counteracts a gas flow due to movements of a substrate holder, according to the well known principles of anti-noise. Ideally, if every movement of the gas would be counteracted, the net gas flow would be reduced to zero, or at least to a very much lower level. Thereto preferably a plurality of loudspeakers is present, in order to be able to correct the influence of spatially complex flows of gas. Note that, more generally speaking, a change in gas pressure without actual flowing of gas may have the same effect as a gas flow, so wherever in this application the term "gas flow" or equivalents like "gas movement" is used, it is to be understood to encompass the term "gas pressure change" and its equivalents.

In another preferred embodiment, the position disturbance correction system comprises at least one of a first substrate holder drive unit and a projection system movement device constructed for moving at least a part of the projection system with respect to the housing, such that a displacement of a target portion with respect to the projection beam due to gas movement is counteracted. Herein, the principle is used that a displacement cannot always be prevented, but as long as knowledge of the occurrence of such a displacement is available, its effect may be counteracted and corrected. "Displacement" means any difference between the actual position and the intended position as required for optimum working of the apparatus. The intended position for optimum working will often relate to the position of the first substrate holder with respect to the projection system, and in particular of the target portion with respect to the projection beam.

The first substrate holder drive device, and/or projection system movement device constructed for moving at least a part of the projection system may be designed and constructed such that a displacement of the target portion with respect to the projection beam is counteracted. The first substrate holder drive device may be any device suitable for moving the first substrate holder over a distance that is required for correcting the disturbance due to the gas flow. Such drive device may comprise piezo-electric motors and so on.

The projection system movement device is designed to correct the position of the projection system with respect to the first substrate holder if at least one of them has been displaced, and notably such that the correct position of the projection beam with respect to a target portion of the first substrate is obtained again. Any appropriate type of movement device is allowed, such as small electro-motors.

Advantageously, the position disturbance correction system comprises a third control unit, the third control unit comprising at least one of at least one gas pressure sensitive device, an interferometer system constructed for measuring gas displacement and/or gas pressure changes at least at the position of at least one movable part, and a position correction information retrieval system constructed for providing previously determined information on position correction as a function of movement of the at least one movable part. In this embodiment the position disturbance correction system comprises a third control device, which is coupled to control any means present for counteracting a displacement of a (first) susbstrate table. In particular, the third control device is coupled to and controls the at least one speaker for moving gas at least at a position of the first substrate holder, and/or to the first substrate holder drive device, and/or to the projection system movement device.

The third control device may be embodied in the first and/or second control device, or may be a separate control device, e.g. in the form of a computer or other processing unit. The third control device advantageously comprises a measuring device constructed for measuring gas displacement, which may comprise a gas pressure sensitive device such as a microphone or pressure gauge. Another third control device comprises a device constructed for measuring pressure variations or actual displacement of gas, such as an interferometer system. Preferably, such an interferometer system comprises at least one measuring beam at a position of the first substrate holder and/or the second substrate holder. This ensures a correct measurement of actual gas displacement at positions were their influence is maximum, and where they can be determined with high accuracy. Advantageously, the interferometer system comprises a measuring beam in the direction of the second substrate holder to the first substrate holder, or vice versa. This allows reliable measurements of displacement of gas in a direction in which it has the maximum impact on e.g. the first substrate holder.

In another advantageous embodiment, the third control device comprises a position correction information retrieval system constructed for providing previously determined information on position correction as a function of movement of the movable part of the measurement system. In this embodiment previously determined information is used to drive position disturbance correction system in order to correct a displacement. An advantage of this embodiment is that the information may be determined in a test run, which allows very precise measurements, since there is no need to perform the measurements in as short a time as possible. Another option would be to calculate the required correction based on model calculations, in which the exact movements of moving parts in the apparatus have been taken into account. Since in an actual apparatus the programmed movements are precisely known, it will be possible to predict gas flows in the apparatus, knowing the properties of the gas, such as density, temperature etc.

A general advantage of using predetermined information is that the control of the position disturbance correction system may be made much quicker, since no time consuming measurements nor processing thereof are required during functioning of the apparatus. In fact, any correction signal may be provided as a feedforward signal, instead of a feedback signal. Note that for any desired pattern of movements a new calculation may be made. Then, even taking into account the time for determining the required information, an improved balance may be found between total production throughput and increased performance, e.g. precision.

In another advantageous embodiment of the invention, there is provided a lithographic projection apparatus, wherein the radiation comprises electromagnetic radiation having a wavelength for which transmissive optics are available, and wherein the position disturbance correction system comprises a vacuum system constructed for decreasing a gas pressure inside the housing, at least at the position of the at least one movable part, preferably to a value of at most 90% of atmospheric pressure, more preferably to at most 50% of atmospheric pressure. In this embodiment, the influence of the gas is decreased by lowering a gas pressure inside the apparatus, to as low a value as possible, and preferably to at most 50% of ambient atmospheric pressure. In a lithographic apparatus with a very low gas pressure, say less than 1 Pa, and furthermore with optimum mechanical damping and decoupling of substrate holders, a very high precision of the exposure may be obtained, and very small details on the substrate may be produced, with a high production rate.

Herein, the expression "for which transmissive optics are available" relates to the following. Generally, lithographic apparatus working with extreme ultraviolet radiation, having a wavelength much shorter than 100 nm, say between 5 and 35 nm, are known. These apparatus work with a vacuum, in order to be at all able to use this type of radiation. For this type of radiation, at present no transmissive optics (i.e. transparent materials for lenses, etc.) are known. For wavelengths of about 126 nm and longer, transmissive optics are known. However, lithographic apparatus working with these wavelengths in practice do not work under vacuum, because up to now there was no need for them to do so. The present inventors have been the first to realize that vacuum offers an advantage for such lithographic apparatus as well, in that they allow the influence of gas movements to be diminished.

A lithographic apparatus of this type, with a lowered gas pressure, may be combined with any appropriate technical measure according to other embodiments of the present invention.

An advantageous device manufacturing method according to the invention comprises providing a lithographic projection apparatus having at least a first and a second movable substrate holder, exposing a first substrate on the first substrate holder to a patterned projection beam of radiation, wherein a gas pressure inside the lithographic projection apparatus is lowered with respect to atmospheric pressure before the step of exposing the first substrate.

Due to the lowered gas pressure, any movements thereof will exert a decreased influence on the position of the first substrate. This in turn improves the definition of the exposure, and decreases overlay errors etc.

Preferably, the gas pressure is lowered to a value of at most 50% of atmospheric pressure, and even more preferably to at most 10% of atmospheric pressure, which even further diminishes the influence of any gas present in the system.

Advantageously, the lithographic projection apparatus is a system according to the present invention, comprising means for further correcting the position of the first substrate holder, in order to further improve the definition performance of the system during exposure.

In principle, lowering of the gas pressure inside the system will improve definition and general performance even when only one moving substrate holder is present. Gas colliding with walls will no longer bounce back to influence the substrate holder, and the inertia of the gas itself will exert less influence. However, if at least a second moving substrate holder is present, such as a second substrate holder for exposing or measuring a second substrate, the effect will be even larger, since the influence of movements of said second substrate holder will also be decreased.

The invention also generally relates to a device manufacturing method comprising providing a lithographic projection apparatus according to the invention with a first substrate, and exposing said first substrate to the patterned beam, wherein during said exposing of the first substrate a position thereof with respect to said projection system is corrected by means of the position disturbance correction system. Use of the position disturbance correction system provides a better exposure result, at least when other moving parts are present in the lithographic projection apparatus. All advantages as described in connection with the system according the invention apply as well.

The invention also relates to a device manufacturing method, comprising providing a lithographic projection apparatus comprising a first exposure system and at least one second system, the exposure system comprising: a radiation system constructed for providing a projection beam of radiation, a support structure for supporting patterning device, the patterning device serving to pattern the projection beam according to a desired pattern, a first substrate holder for holding a substrate, a projection system constructed for projecting the patterned beam onto a target portion of the substrate, a positioning device for positioning the substrate holder relative to the projection system and a first control unit constructed for controlling said positioning device. The second system comprises at least one of a corresponding second exposure system and a measurement system, the measurement system comprising: a measurement device constructed for projecting onto a target portion of the second substrate a measurement beam for measuring a surface property and/or a substrate marker position of said target portion; and a second substrate holder for holding a second substrate, a second control unit constructed for moving a movable part of the measurement system such that the second substrate is movable with respect to the measurement beam, providing a first substrate and a second substrate, projecting the patterned beam of radiation onto a target portion of the first substrate, measuring a surface property and/or a marker position of the second substrate, wherein, during measuring at least one of a surface property and a substrate marker position of said target portion, at least one of a speed and an acceleration of the second substrate holder is reduced to a speed value, an acceleration value, respectively, which is smaller than a predetermined maximum speed value, a predetermined maximum acceleration value, respectively, when a distance between the first substrate holder and the second substrate holder is smaller than a predetermined minimum distance value.

The advantages as described in connection with the corresponding lithographic projection apparatus apply as well, and will not be repeated here for brevity.

The invention also relates to a device manufacturing method comprising the steps of: providing a lithographic projection apparatus comprising an exposure system and a measurement system, the measurement system comprising: a substrate holder for holding a substrate, a measurement device constructed for projecting onto a target portion of the second substrate a measurement beam for measuring at least one of a surface property and a substrate marker position of said target portion, and a control unit constructed for moving a movable part of the measurement system such that the substrate is movable with respect to the measurement beam, providing a substrate, projecting the patterned beam of radiation onto a target portion of the substrate, measuring at least one of a surface property and a marker position of the substrate, wherein the substrate is accelerated during at least a part of the step of measuring the at least one of a surface property and substrate marker position.

Up to now, the measuring of a surface property or a substrate marker position has always taken place during a movement of the second substrate holder in which the velocity was substantially constant. This allowed a simple measurement set-up, in which scanning of the surface meant simply measuring the surface property with a certain fixed frequency. It also had the advantage that no accelerations were required during measuring, enabling accurate positioning during the measurement. However, a disadvantage was that the distance traversed by the substrate holder during acceleration to the desired speed is lost for the measurement: no measurement is performed when the second substrate holder is in that part of its trajectory. The same holds for the part relating to negative acceleration, or slowing down. In practice, another part of the trajectory was not used for measuring, notably the part during which the movement of the substrate holder was allowed to "settle". All this had the additional disadvantage that, in order to obtain a desired throughput of measured substrates, the required speed was relatively high. The inventors found that this caused position disturbances of the first substrate holder, as discussed above.

By means of the measure proposed above, i.e. the second substrate is accelerated during at least a part of the step of measuring the surface property, it is possible to use all of the available space for measurement purposes. It suffices to either control a measurement frequency in order to obtain a regular grid of measurement positions, and/or to interpolate the surface property for the intermediate positions on the substrate if the measurement frequency is not changed. It should be noted that it is advantageous to use all available space, since in lithographic apparatus in general, a small volume is a very important design criterion. Alternatively, if the space allowed for the measurement substrate stage remains the same, the minimum distance between the substrate stages can be increased because a smaller run-in length is required.

Advantageously, each measurement contains information suitable for deriving the actual position at the time of said measurement. This information may be e.g. the count of the measurement. Given the measurement frequency and the velocity as function of time, the actual position may be inferred. The information may also be a direct measurement of position, e.g. through coupling with a position determining system, such as an interferometer.

An additional advantage is that, to obtain a desired throughput, it is now possible to select a lower (average) speed and/or acceleration for the measurement, since there is relatively more effective time available to measure or scan the complete surface of the substrate. No time is lost for acceleration or deceleration, or put more precisely: the time for acceleration and deceleration is also used for measuring.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, liquidcrystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. Further, the substrate referred to herein may be processed, before or after exposure, in for example a track (a tool that typically applies a resist to a substrate and develops the exposed resist) or a metrology or inspection tool. Where applicable, the disclosure herein may be applied to such and other substrate processing tools.

The terms "radiation" and "beam" used herein encompass all types of electromagnetic radiation, including ultraviolet (UV) radiation (e.g. having a wavelength of 365, 248, 193, 157 or 126 nm) and extreme ultra-violet (EUV) radiation (e.g. having a wavelength in the range of 5–20 nm), as well as particle beams, such as ion beams or electron beams.

The term "patterning device" used herein should be broadly interpreted as referring to a mechanism that can be used to impart a projection beam with a pattern in its cross-section such as to create a pattern in a target portion of the substrate. It should be noted that the pattern imparted to the projection beam may not exactly correspond to the desired pattern in the target portion of the substrate. Generally, the pattern imparted to the projection beam will correspond to a particular functional layer in a device being created in the target portion, such as an integrated circuit.

Patterning mechanisms may be transmissive or reflective. Examples of patterning device include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions; in this manner, the reflected beam is patterned. In each example of patterning device, the support structure may be a frame or table, for example, which may be fixed or movable as required and which may ensure that the patterning device is at a desired position, for example with respect to the projection system. Any use of the terms "reticle" or "mask" herein may be considered synonymous with the more general term "patterning device".

The term "projection system" used herein should be broadly interpreted as encompassing various types of projection system, including refractive optical systems, reflective optical systems, and catadioptric optical systems, as appropriate for example for the exposure radiation being used, or for other factors such as the use of an immersion fluid or the use of a vacuum. Any use of the term "lens" herein may be considered as synonymous with the more general term "projection system".

The illumination system may also encompass various types of optical components, including refractive, reflective, and catadioptric optical components for directing, shaping, or controlling the projection beam of radiation, and such components may also be referred to below, collectively or singularly, as a "lens".

The lithographic apparatus may be of a type having two (dual stage) or more substrate holders (and/or two or more mask tables). In such "multiple stage" machines the additional tables may be used in parallel, or preparatory steps may be carried out on one or more tables while one or more other tables are being used for exposure.

The lithographic apparatus may also be of a type wherein the substrate is immersed in a liquid having a relatively high refractive index, e.g. water, so as to fill a space between the final element of the projection system and the substrate. Immersion liquids may also be applied to other spaces in the lithographic apparatus, for example, between the mask and the first element of the projection system. Immersion techniques are well known in the art for increasing the numerical aperture of projection systems.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 5b shows examples of the corresponding acceleration a, velocity v and position x during one part of the trajectory of FIG. 5a.

DETAILED DESCRIPTION

First Embodiment

Figure 1:
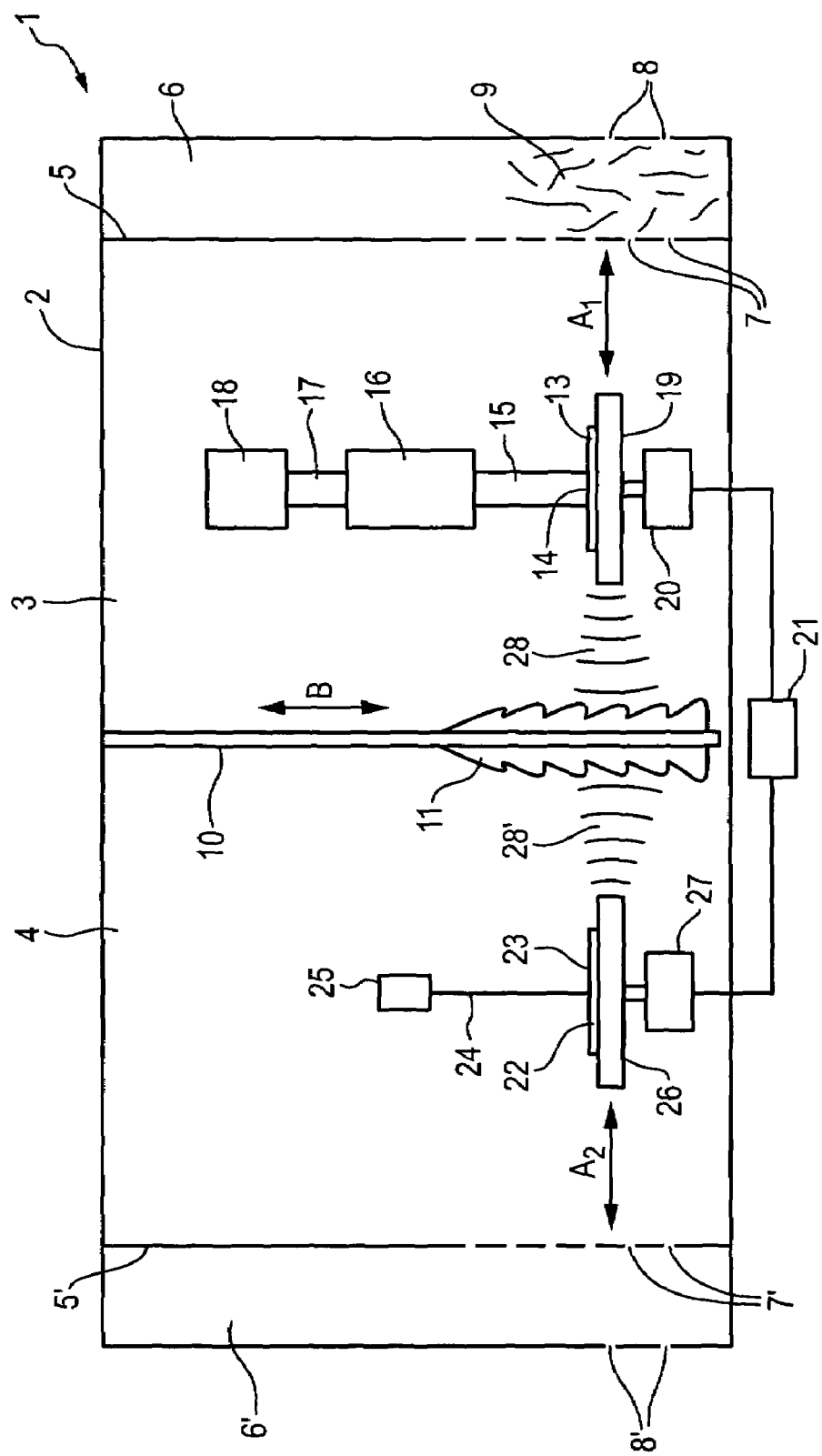
FIG. 1 is a schematic cross-sectional view of a first embodiment of the lithographic projection apparatus according to the invention.

FIG. 1 is a schematic cross-sectional view of a first embodiment of the lithographic projection apparatus according to the invention. The lithographic projection apparatus is generally indicated with reference numeral 1. The system comprises a housing 2, which is subdivided into a first compartment 3 and a second compartment 4. The first and second compartment 3, 4 are separated from spaces 6, 6' respectively, by means of separating walls 5, 5' respectively, in which separating walls there are provided apertures 7, 7'. Further apertures 8, 8' connect the spaces 6, 6' to the outside world. In space 6 there has been provided damping material 9. The first compartment 3 and the second compartment 4 may be separated by means of a movable wall 10, which is provided with additional damping material 11.

In the first compartment 3 there is provided a first substrate 3, a target portion 14 of which is illuminated by a patterned radiation beam 15 provided by a projection system 16, which in turn receives a beam of radiation 17 from a source 18.

The first substrate 3 is held in a first substrate holder 19, which is movable in ate least the direction of arrow $A_1$ by means of first substrate holder drive mechanisms 20, which is connected to and controlled by control unit 21.

In the second compartment 4, there is provided a second substrate 22, having a surface 23 which is measured by means of a measuring beam 24 provided by measuring mechanisms 25.

The second substrate 23 is held on a second substrate holder 26 which is movable in at least the direction indicated by arrow $A_2$ by means of second substrate holder drive mechanisms 27, which is also connected to control unit 21.

The embodiment schematically shown in FIG. 1 comprises a combination of different features according to the invention, all of which need not be present at the same time in order to achieve the effect according to the invention. In particular, the embodiments shown relate to two stage apparatus, even though these are not always shown in much detail. However, the invention also relates to apparatus with only one movable stage (first substrate holder).

The system 1 as shown comprises an exposure section in the first compartment 3 and a measuring section in the second compartment 4. The number of sections is however not limited to two, but there may be a single section, and also three or more sections.

The housing 2 may be any housing suitable for accommodating lithographic stages. In particular the housing 2 will be a kind of box which is substantially closed on all sides in order to be able to control the quality of the atmosphere inside the housing 2. In particular, the inner atmosphere will be kept substantially dust-free. Thereto, the housing 2 will often be purged with gas by means of gas purge mechanisms (not shown).

In first compartment 3, an exposure stage is shown schematically, in which a first substrate 13, in particular a target portion 14 thereof, is exposed to a patterned radiation beam 15. The patterned beam 15 is emitted by a projection system 16, which in turn receives radiation 17 from source 18. The source 18 and the projection system 16 may be any device suitable for providing a patterned beam 15. Since they do not form part of the true invention, they are not shown in any detail.

In order to fully expose the first substrate 13 to the patterned radiation beam 15, different target portions 14 must be illuminated. Thereto, the first substrate 13 is moved with respect to the patterned radiation beam 15 by means of a movable first substrate holder 19. One of the possible directions of movement is indicated by means of arrow $A_1$ in FIG. 1. Another possible direction of movement will be in the direction perpendicular to the plane of the drawing (not indicated). The first substrate holder 19 is movable by means of first substrate holder drive mechanisms 20, which may be controlled by means of control unit 21.

The first substrate holder drive mechanisms 20 may be any suitable actuator, such as a Lorenz-type or electromagnetic actuators or the like. The movements of the first substrate holder 19 will induce movements of the gas inside the first compartment 3, as indicated by "shock waves" 28. Direct interaction, or friction, of the first substrate holder 19 with the gas inside the first compartment 3, or friction with moving gas that has bounced off the walls of the housing 2, such as separating wall 5, may cause a disturbance of the position of the first substrate holder 19, and hence of the first substrate 13, with respect to the patterned radiation beam 15. According to the invention, one or more position disturbance correction system are present in order to ensure an improved position accuracy.

A first such mechanisms present is apertures 7, through which moving gas may escape to a first space 6. Depending on the relative size of the apertures 7, the dimensions of the first space 6 and the distance to the first substrate holder 19, the apertures 7 will function as a kind of "black hole" for the gas waves or 'shock waves', which will substantially damp out the movements thereof.

In order to further increase the damping power of the first space 6, said space may contain damping material 9, which may come in the form of e.g. fluffy material such as fibers or plastic foam. Such damping materials will very effectively damp every movement of the gas.

Another possible measure is providing second apertures 8, 8' in an outer wall of the housing 2. Since these second apertures open to the environment of the system 1, any gas wave striking such a second aperture is substantially 100% effectively absorbed. In order to maintain a controlled atmosphere, it is advantageous to provide second apertures 8, 8' in the case wherein the inside of the system 1, in particular of the first compartment 3, is maintained at a gas pressure which is higher than the gas pressure outside the system 1, the first compartment 3, respectively.

Yet another possible position disturbance correction system is a movable wall 10, which is shown to be movable in the direction of arrow B. A first effect of the movable wall is to increase the effective volume of the first compartment 3 when the movable wall 10 is moved upwards (in the drawing) in order to fully connect the first compartment 3 and the second compartment 4 with each other. Especially in the case wherein no parts are moving in the second compartment 4, the increased volume will act more effectively to damp any gas movement. On the other hand, if moving parts are present in the second compartment 4 (to be described below), then moving the movable wall 10 into a position in which the second compartment 4 is effectively disconnected from the first compartment 3 ensures that any movement inside the second compartment 4 will not influence compartment 3, in particular the first substrate holder 19 therein.

The movable wall 10 may be e.g. a curtain, a diaphragm etc., and may be made from any suitable, in particular sufficiently rigid material. Advantageously, the material of the movable wall 10 is also acoustically damping, such as cloth-like material.

Advantageously, the movable wall 10 is provided with additional damping material 11, which may be similar to the damping material 9, although it will advantageously be more compact and stable.

As shown in FIG. 1, the second compartment 4 is provided with many similar position correction disturbance mechanisms, in particular a space 6' with first apertures 7' and second apertures 8', as well as damping material 11 on the corresponding side movable wall 10 facing the second compartment.

In the second compartment 4, there is shown a measuring stage, comprising a measuring mechanisms 25 emitting a measuring beam 24 which measures a surface 23 of a second substrate 22.

The second substrate 22 is held on a second substrate holder 26 which is moveable in at least the direction indicated by arrow $A_2$ by means of second substrate holder drive mechanisms 27. Movements of the second substrate holder 26 may cause gas movements as indicated by 28'.

Second substrate holder drive mechanisms 27 are connected to and may be controlled by control unit 21. Advantageously, the movements of both the first substrate holder drive mechanisms 20 and of the second substrate holder drive mechanisms 27 are controlled in mutual dependence. This will be elucidated further below.

Second Embodiment

Figure 2:
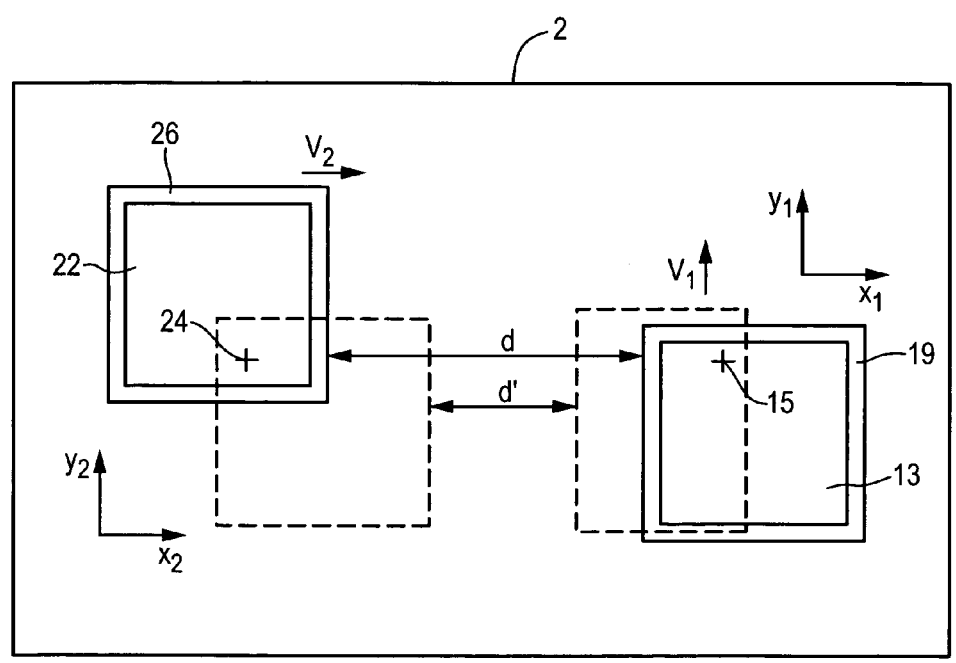
FIG. 2 shows a schematical plan view of an embodiment of the lithographic projection apparatus according to the invention.

FIG. 2 shows a schematical plan view of another embodiment of the lithographic projection apparatus according to the invention. Similar parts are denoted by the same reference numerals throughout the drawings. In particular, the cross 15 indicates the center of the patterned projection beam, while the cross 24 indicates the measuring beam.

Furthermore, first substrate holder 19 and second substrate holder 26 are shown in a first position, drawn in solid lines, and are furthermore shown in second positions, drawn in dashed lines.

In the first positions, the first substrate holder has an momentary velocity indicated by arrow V1, while the second substrate holder has a momentary velocity indicated by arrow V2. The minimum distance between the first and the second substrate holder is indicated by arrow D. In the second positions, the minimum distance is indicated by arrow D'.

The two substrate holders 19, 26 are shown in two extreme positions. In the first positions, the distance d is maximum, and the mutual influence of the two substrate holders 19, 26 is a minimum. On the contrary, in the second positions, the distance d' is minimum and the mutual influence is a maximum. During normal operation of the system 1 as shown, both substrate holders will perform more or less complex movements, which sometimes bring them close together and sometimes move them further apart. Up to now, these movements have never been co-ordinated, and may have caused too much influence through gas movements.

However, the influence of movements of the second substrate holder 26 furthermore depends on the momentary velocity V2, and also on changes thereof (acceleration, jerk). Hence, advantageously, the momentary velocity V2 and or acceleration of the second substrate holder 26 is low when the distance between the second substrate holder 26 and the first substrate holder 19 is smaller than a certain predetermined distance. Advantageously, the distance between the two substrate holders is kept as large as possible, preferably at least equal to the average distance. The latter situation may for example be obtained by having the two substrate holders 19, 26 perform a completely synchronized movement. However, this is not always possible since the objectives for moving the substrate holders may be different.

Note that the two measures, viz. keeping the distance between the two substrate holders as large as possible and decreasing the velocity (and changes thereof) of the second substrate holder 26 when the distance to the first substrate holder 19 falls below a predetermined value, may be combined in order to further improve the position correction of first substrate holder 19.

Third Embodiment

Figure 3:
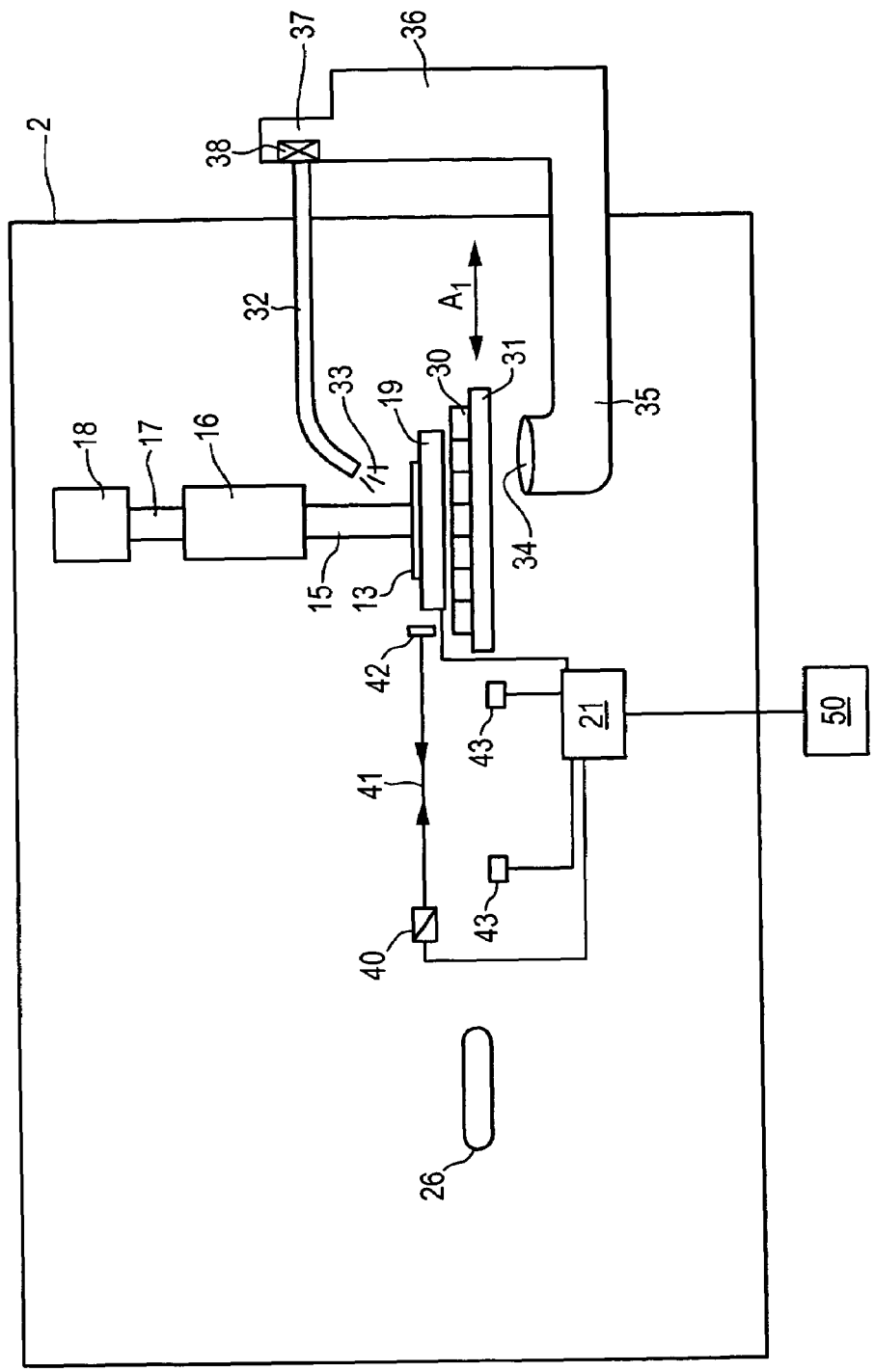
FIG. 3 shows yet another embodiment of the lithographic projection apparatus according to the invention, in a schematic cross-sectional view.

FIG. 3 shows yet another embodiment of the lithographic projection apparatus according to the invention, in a schematic cross-sectional view. Again, similar parts are denoted by equal reference numerals. Herein, the second stage is indicated only in the form of the second substrate holder 26.

Note that the shape of the substrate holder 26 has an aerodynamical character in order to cause as little motion in the surrounding gas as possible. Similarly, first substrate holder 19 also has an aerodynamical shape, much to the same effect. In practice, the aerodynamical shape often relates to rounded off or bevelled corners, although other adaptations of the shapes are also possible.

In FIG. 3, first substrate holder 19 is moved by means of a planar motor. Thereto, the first substrate holder 19 comprises one or more coils, not indicated any further. Below the substrate holder 19 a number of magnets 30 is arranged, in a checkers-like pattern. For support, a magnetically conductive backing plate 31 is provided. First substrate holder 19 may be moved with respect to the magnets 30 in the direction of a.o. $A_1$. This may be achieved by suitably actuating the various coils in table 19. Thereto, these coils are connected to and controlled by control unit 21. Such a planar motor may be made relatively flat, thereby providing only a small cross-sectional area to the moving gas. Thus, the first substrate holder 19 will be subject to smaller forces due to gas motion, and will also create less gas motion. Similarly, table 26 can be moved by a planar motor as well.

Furthermore, there is optionally provided a gas supply tube 32, which ejects a gas flow 33, which flows past first substrate holder 19. The gas flow 33 is sucked away through opening 34 of gas exhaust tube 35, which is connected to gas tank 36, which in turn is connected to gas conditioning mechanisms 37, in which pump 38 pumps the gas through to supply tube 32.

The gas flow 33 may be a flow of conditioned gas, e.g. having a certain composition and temperature, and in particular a very low particle count (i.e. it is relatively dust-free). Although it is possible, and common, to let the gas in gas flow 33 leak away via openings in the housing 2, it is advantageous to actively suck away the gas via opening 34 in order to prevent the build-up of a too high pressure inside the housing 2, or the compartments. Especially in the vicinity of the first substrate holder 19, a too high gas pressure, in particular a pressure above atmospheric pressure, causes the first substrate holder 19 to be more susceptible to movement of the surrounding gas. If the pressure of the gas is lowered by sucking away the gas via exhaust tube 35, the influence is decreased. The position of the opening 34 is advantageously near the first substrate holder 19, although this is not necessary. A position near the first substrate holder 19 allows effective sucking of the gas, minimizing the risk of any gas pockets. Also, gas movements created by tables 19 and 26 are absorbed by the system 34, 35, 36, thereby decreasing the influence of gas motions on table 19.

In a different embodiment, there is no active gas supply, but any gas present in the housing 2 is still sucked away via opening 34 by pump 38. Thereto, the pump 38 may vent the gas to the environment (not indicated any further). Actively sucking away gas without supplying new gas will cause the pressure inside the housing to drop. In particular, the gas pressure may be lower than atmospheric pressure, advantageously as low as possible. The lower the gas pressure, the smaller the influence caused by movement by gas inside the housing 2.

Yet another means for correcting a position disturbance is an interferometer system, comprising an interferometer 40 which emits a laser beam 41, which is reflected by a mirror 42 near the first substrate holder 19. The mirror 42 should be a fixed mirror, but yet be near to the movable part(s), in this case the first substrate holder, in order to provide relevant data on the gas pressure changes. The interferometer system serves to measure pressure differences of the gas, advantageously between the first substrate table 19 and the second substrate holder 26, although this is not the only possible path to measure. The measured pressure differences are an indication of motion of the gas along the path.

As is known in the art, gas pressure difference cause changes in the refractive index and hence in the optical path length of laser beam 41, which may be measured by means of interference patterns in interferometer 40. The signal of interferometer 40 may be coupled to control unit 21, which may then calculate a position disturbance of first substrate holder 19. A position correction may then be obtained by suitably actuating the first substrate holder drive mechanism, in this case the planar motor 30, 31. Note that since the planar motor 30, 31 is well-known in the state of the art, it will not be elucidated any further in this application.

Yet another means for correcting a position disturbance of the first substrate holder 19 is shown in the form of gas gauges 43. The gas gauges 43 serve to measure e.g. gas pressure or gas velocity. On the basis of the measured values, which values are fed to the control unit 21, an effect of gas motion on the position of the first substrate holder 19 may be calculated by control unit 21. Control unit may then carry out a correction of the position of first substrate holder 19 via suitably actuating first substrate holder drive mechanism. Gas gauges 43 may be any known gas gauge, e.g. microphones, manometers or any other kind of pressure gauge.

Yet another measure to correct a disturbance of the position of the first substrate holder 19 is indicated only schematically by means of position information retrieval system 50. Position information retrieval system 50 contains information about disturbance of the position of the first substrate holder 19 as caused by known movements of the second substrate holder 26. Such information may e.g. have been measured in an earlier, separate run, in which e.g. any position has been measured very carefully. The information may be used to provide a feedforward signal to control unit 21 in order to counteract the position disturbance caused by movements of second substrate holder 26, advantageously at the very moment that said disturbance is caused. This will effectively minimize the net position disturbance.

Note that in the above the position of parts inside or outside the housing 2 is pretty much random. The actual position of all parts may be inside the housing 2, whenever desired. Furthermore, control unit 21 may comprise a computer or any other system capable of receiving and processing information. Position information retrieval system 50 may likewise comprise a computer system, or a data storage and retrieval system, such as a hard disk unit, a CD-ROM unit etc.

Fourth Embodiment

Figure 4:
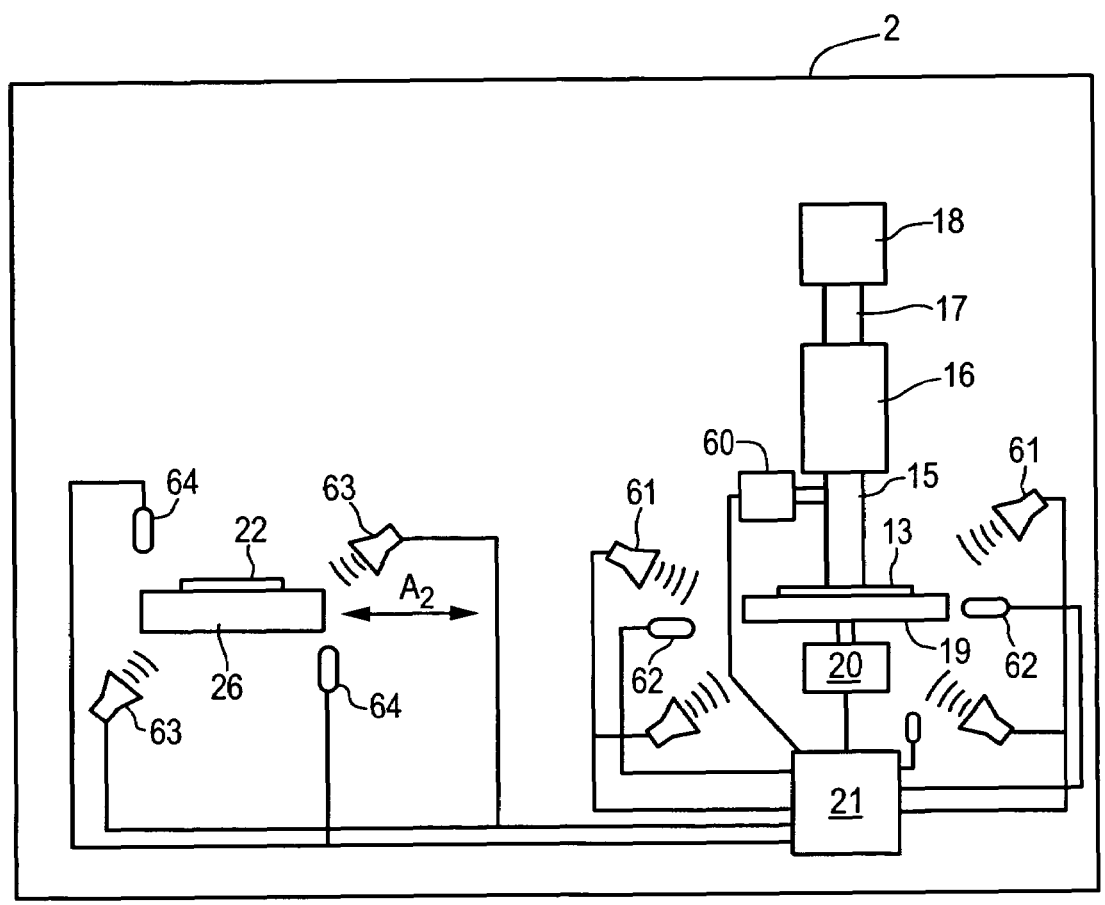
FIG. 4 shows a cross-sectional view of yet another embodiment of the lithographic projection apparatus according to the invention.

FIG. 4 shows a cross-sectional view of yet another embodiment of the lithographic projection apparatus according to the invention. Herein, 60 denotes a projection system movement mechanism, 61 indicate first loudspeakers, 62 are first microphones, 63 are second loudspeakers, and 64 are second microphones.

In the embodiment shown, projection system movement mechanism 60 are constructed for moving the projection system 16, such that the patterned radiation beam 15 is moveable with respect to the first substrate 13. Projection system movement mechanism 60 may comprise any suitable type of actuator, such as micro-motors, piezo-electrical motors etc. They may be designed and constructed to move the projection system 16 in a parallel fashion, or change its tilt with respect to the first substrate 13, or a combination thereof. The projection system movement mechanism 60 are connected to and controlled by control unit 21. Information for controlling the projection system movement mechanism 60 may be provided to control unit 21 by means of previously determined position disturbance corrections, or may be provided by means of a measuring system.

Yet another example of a position disturbance correction system is formed by the first loudspeakers 61, optionally combined with the microphones 62. The loudspeakers emit pressure waves in the gas inside the housing 2, which pressure waves will counteract gas movements due to movements of the second substrate holder 26, e.g. in the direction of arrow $A_2$.

The first loudspeakers 61 are connected to control unit 21 for receiving control instructions. Note that here, as in all other drawings, the control unit 21 are shown as a single unit although it is also possible that there are separate control unit for various position disturbance correction system.

The number of speakers shown, i.c. four, is an arbitrary number. Obviously at least one loudspeaker must be present, but the number has no upper limit. A number of four loudspeakers, however, will give a satisfactory performance by emitting gas pressure waves from four different directions towards first substrate holder 19.

Optionally there are provided one or more first microphones 62 or other types of gas pressure gauges. Although three first microphones are shown, the number is not limited thereto, but may be as small as one, or theoretically as many as a few dozens. The higher the number of microphones, the more precise the obtained information will be. Although microphones are shown as gas pressure gauges, any other kind of measuring instrument that provides such information is also suitable, such as pressure meters (piezo-electrical meters, mano-meters) etc. The first microphones 62 are also connected to control unit 21, such that the control unit 21 are able to process the measured information.

The first loudspeakers 61 and the first microphones 62 are shown located in the vicinity of the first substrate holder 19. They serve to correct and damp out gas movements near the first substrate holder 19. It is also possible to counteract such gas movements near their origin, viz. the second substrate holder 26. Movements of the second substrate holder 26, e.g. in the direction of arrow $A_2$, may be detected by means of second microphones 64, which are connected to control unit 21 for processing measured information. Control unit 21 may control second loudspeakers 63, which are able to emit gas pressure waves, or sound, that will counteract gas movements that originate in the vicinity of second substrate holder 26. It may be advantageous to counteract gas movements near their origin, since any residual gas movement will then further fade out before they reach the first substrate holder 19. The position precision to be obtained thereby is increased even further.

The position disturbance correction system that use microphones and loudspeakers is known in the state of the art as an "anti-noise" system. Any hardware or software known in this area that is useful for increasing precision may be applied in this embodiment as well.

Figure 5A:
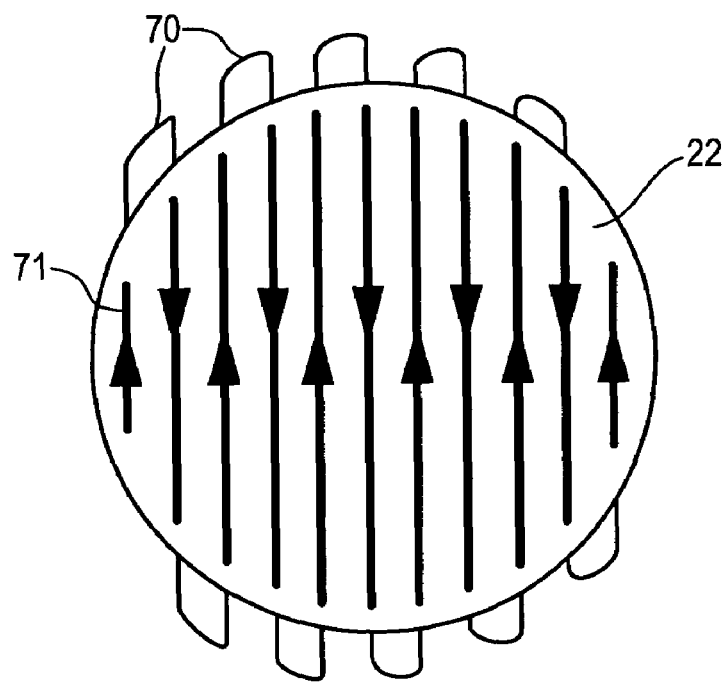
FIG. 5a shows an exemplary measuring trajectory over a first substrate.
Figure 5B:
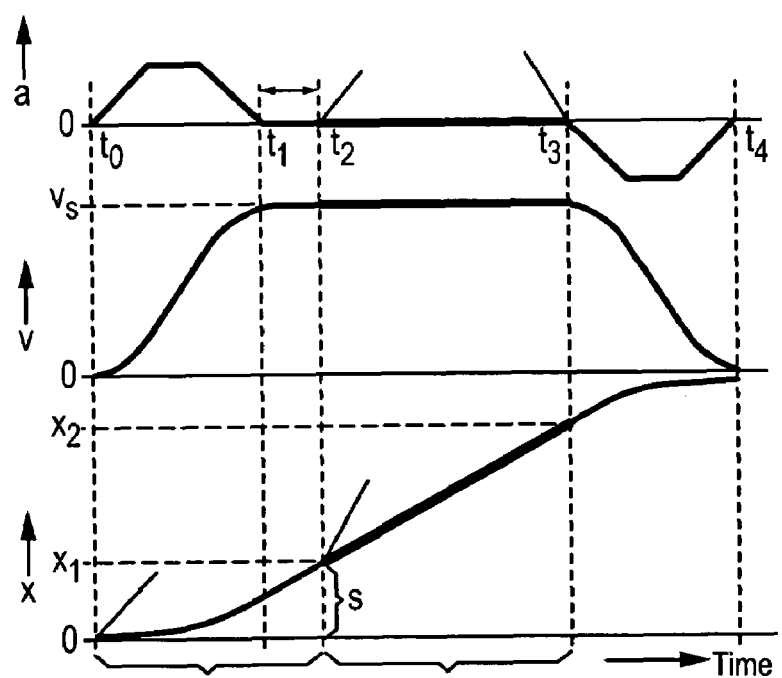

FIG. 5a shows an exemplary measuring trajectory over a substrate, and FIG. 5b shows examples of the corresponding acceleration a, velocity v and position x during one part of the trajectory of FIG. 5a.

FIG. 5a shows a schematical plan view of the trajectory of a measuring beam across the surface of a (second) substrate 22. The trajectory comprises a number of parallel strokes 71, connected by reversal motions 70. The direction of movement in every stroke has been indicated by means of an arrow. The possible trajectories for scanning the surface of substrate 22 are not limited hereto, and the trajectory shown is only an example.

Up to now, it has been common to accelerate the substrate 22, together with substrate holders etc., to the desired measuring velocity only when the measuring beam is in the reversal motion 70. During all of the actual measuring trajectories, the velocity was kept substantially constant. At the end of the trajectory, the substrate was decelerated and reversed. Note that usually the substrate is moved with respect to a fixed measuring beam.

A disadvantage of this method is that the space that is required for the reversal motions is relatively large. The method according to the invention aims at decreasing this volume requirement, and thereto is characterized by the fact that during measurement of the surface of the substrate 22 the velocity of the substrate with respect to the measuring beam is changed.

In practice, this means that only a very small space is needed for reversing the motion, since as soon as the measuring beam strikes the surface of the substrate 22, measuring can begin.

FIG. 5b shows an example of values of the acceleration a, velocity v and position x during one straight part of the trajectory of FIG. 5a. In fact, the graphs shown may be used for elucidating the values during measuring according to the state of the art, and for elucidating the values according to measuring with the method according to the present invention.

In the figure, during the time between $t_0$ and $t_1$ an acceleration is applied to the substrate 22 in order to impart a certain velocity to the substrate. The velocity v increases from zero to a certain value $v_s$, the scan velocity. During time $t_1$ to $t_2$ the system is allowed to settle, in order for the velocity value to stabilize. The actual measurement is performed between time $t_2$ and $t_3$. In other words, the part of a surface of the substrate 22 is traversed by the measuring beam between time $t_2$ and time $t_3$. In the graph of x as a function of time it can be seen that the actual scan takes place between $x_1$ and $x_2$. The distance indicated by bracket s, the run-in trajectory, is the distance which would normally be lost for measuring, and would be part of the reversal motion.

According to the present invention, measuring is simply started much earlier, for example at zero velocity, at $x=0$. Obviously, in this case, the actual scan range will not be between $x=x_1$ and $x=x_2$, but between $x=0$ and $x=x_{max}$ (not further indicated). Nevertheless, it will be obvious that the run-in trajectory is substantially absent if measuring starts immediately. In this case, measuring during the first part of the trajectory, i.e. between $x=0$ and $x=x_1$, the velocity changes, as can be seen in the figure, and hence the measured values must be interpreted correctly. This may however be done by means of simple mathematics, which may for example be embodied in a computer program for evaluation of the measured values as function of measuring time.

A specific advantage of allowing the measuring velocity to be non-constant is that it is possible to measure from edge to edge of the substrate 22, wherein the reversal motion (referring to FIG. 5a) takes place on or very near the circumference of the substrate 22. This requires the least amount of space, and the least amount of time. Additional advantages are a larger distance between tables 19 and 26, hence decreasing the influence one has on the other due to moving gas; and a possibility to use lower maximum accelerations and velocities for the measurement stage while maintaining a high throughput.

Whilst specific embodiments of the invention have been described above, it will be appreciated that the invention may be practiced otherwise than as described. The embodiments described above may, instead, be implemented in different embodiments of software, firmware, and hardware in the entities illustrated in the figures.

As such, the description is not intended to limit the invention. The configuration, operation, and behavior of the present invention has been described with the understanding that modifications and variations of the embodiments are possible, given the level of detail present herein. Thus, the preceding detailed description is not meant or intended to, in any way, limit the invention—rather the scope of the invention is defined by the appended claims.

What is claimed is:

1. A lithographic projection apparatus, comprising:
    a first exposure system having at least one movable part, said at least one movable part being located within a housing, said housing including an additional movable part that is movable by a second control unit, said first exposure system including:
    (i) a radiation system configured to provide a beam of radiation;
    (ii) a support structure configured to support a patterning device that serves to impart the beam of radiation with a pattern in its cross-section;
    (iii) a first substrate holder for holding a substrate;
    (iv) a projection system configured to project the patterned beam onto a target portion of said substrate;
    (v) a positioning device configured to position said first substrate holder relative to said projection system;
    (vi) a first control unit configured to control said positioning device; and
    (vii) a position disturbance correction system constructed to counteract a disturbance of a position of said first substrate holder, wherein the disturbance is caused by gas movements induced by movement of said at least one movable part,
    wherein, when a distance between said first substrate holder and said additional movable part is less than a predetermined minimum distance value, said position disturbance correction system being configured to reduce a speed and/or an acceleration of said additional movable part to a respective speed value and/or acceleration value, in which the respective speed value and/or acceleration value is less than a predetermined maximum speed value and/or maximum acceleration value.

2. The lithographic projection apparatus of claim 1, wherein said at least one movable part comprises at least one of said support structure and said first substrate holder.

3. The lithographic projection apparatus of claim 1, wherein said additional movable part comprises at least one of a second exposure stage that has at least a movable second substrate holder and a measuring stage for measuring a property of a substrate that has at least one of a movable substrate measuring table and a movable measuring unit.

4. The lithographic projection apparatus of claim 3, wherein said position disturbance correction system comprises a separation wall, which can be positioned between said additional movable part and at least one of said first substrate holder and said patterning device.

5. The lithographic projection apparatus of claim 4, wherein said separation wall comprises an acoustic damping material.

6. The lithographic projection apparatus of claim 4, wherein said first substrate holder is located in a first space and said additional movable part is located in a second space within said housing, and wherein said separation wall is movable into a first position in which said separation wall substantially seals said first space with respect to said second space, and moveable into a second position when swapping of said first and second substrate holder is enabled.

7. The lithographic projection apparatus of claim 1, wherein at least one of said first and second control unit are designed to maintain a predetermined minimum distance between said first substrate holder and said additional moving part at least during projecting of the patterned beam.

8. The lithographic projection apparatus of claim 7, wherein the predetermined minimum distance is equal to at least 50% of a time averaged distance between said first substrate holder and said additional movable part at least during projecting of the patterned beam.

9. The lithographic projection apparatus of claim 8, wherein the predetermined minimum distance is substantially equal to said time averaged distance.

10. The lithographic projection apparatus of claim 1, wherein the maximum speed value is less than a time averaged value of the speed of said additional movable part during projecting of the patterned beam onto said substrate in said first exposure system.

11. The lithographic projection apparatus of claim 1, wherein the maximum acceleration value is less than a time averaged absolute value of the acceleration of said additional movable part during projecting of the patterned beam onto said substrate in said first exposure system.

12. The lithographic projection apparatus of claim 1, wherein a wall, which at least partly surrounds a first space in which said movable part is located, comprises at least one aperture, and wherein said first space communicates with a second space behind said wall, as seen from the movable part.

13. The lithographic projection apparatus of claim 12, wherein said second space comprises the environment outside the lithographic projection apparatus.

14. The lithographic projection apparatus of claim 1, further comprising a gas transport mechanism configured to transport a flow of gas pass said substrate during projection of the patterned beam onto said substrate, and wherein said position disturbance correction system comprises gas suction mechanism configured to suction gas out of the flow after the flow has passed said substrate.

15. The lithographic projection apparatus of claim 1, wherein said position disturbance correction system comprises a planar motor for moving said at least one movable part.

16. The lithographic projection apparatus of claim 1, wherein said position disturbance correction system comprises at least one loudspeaker for moving gas at least in a space surrounding said movable part.

17. The lithographic projection apparatus of claim 1, wherein said position disturbance correction system comprises at least one of a first substrate holder drive unit and a projection system movement device constructed for moving at least a part of said projection system with respect to said housing, such that a displacement of a target portion with respect to the projection beam due to gas movement is counteracted.

18. The lithographic projection apparatus of claim 1, wherein said position disturbance correction system comprises a third control unit comprising, at least one of a gas pressure sensitive device and an interferometer system configured to measure at least one of gas displacement and a gas pressure changes, and a position correction information retrieval system configured to provide previously determined information on position correction as a function of movement of said at least one movable part of the measurement system.

19. The lithographic projection apparatus of claim 18, wherein said third control unit comprises an interferometer system constructed for measuring at least one of gas displacement and gas pressure changes in a direction towards said at least one movable part.

20. The lithographic projection apparatus of claim 1, wherein said radiation comprises electromagnetic radiation having a wavelength for which transmissive optics are available, and wherein said position disturbance correction system comprises a vacuum system constructed for decreasing a gas pressure inside said housing, at least at the position of said at least one movable part.

21. The lithographic projection apparatus of claim 20, wherein said vacuum system is constructed for decreasing said gas pressure to a value of at most 90% of atmospheric pressure.

22. The lithographic projection apparatus of claim 20, wherein said vacuum system is constructed for decreasing said gas pressure to a value of at most 50% of atmospheric pressure.

23. A device manufacturing method for an exposure system having at least one moving part, comprising:

projecting a patterned beam of radiation onto a target portion of a substrate; and correcting a disturbance of a position of said substrate during said projecting, wherein the position disturbance is caused by gas movements induced by movement of said at least one movable part.

24. The device manufacturing method of claim 23, further comprising suctioning gas out of a flow of gas movements after the flow has passed said substrate.

25. The device manufacturing method of claim 23, further comprising counteracting a displacement of the target portion with respect to the patterned beam due to gas movement by use of at least one of a substrate holder drive unit and a projection system movement device constructed for moving at least a part of said projection system with respect to a housing, in which it is disposed.

26. The device manufacturing method of claim 23, further comprising retrieving previously determined information on position correction as a function of movement of said at least one movable part of the measurement system.

27. A lithographic projection apparatus, comprising:
a radiation system configured to provide a beam of radiation;
a support structure configured to support a patterning device that serves to impart the beam of radiation with a pattern in its cross-section;
a substrate holder for holding a substrate;
a projection system configured to project the patterned beam onto a target portion of said substrate;
a positioning device configured to position said substrate holder relative to said projection system; and
a position disturbance correction system that counteracts gas movement-induced disturbances of a position of said substrate holder.

28. A lithographic projection apparatus, comprising:
a radiation system configured to provide a beam of radiation;
a support structure configured to support a patterning device that serves to impart the beam of radiation with a pattern in its cross-section;
a substrate holder for holding a substrate;
a projection system configured to project the patterned beam onto a target portion of said substrate;
a positioning device configured to position said substrate holder relative to said projection system; and
means for counteracting a disturbance of a position of said substrate holder, wherein the positional disturbance is caused by gas movements.

* * * * *